US010480856B2

(12) United States Patent
Massari

(10) Patent No.: US 10,480,856 B2
(45) Date of Patent: Nov. 19, 2019

(54) DEVICE FOR DRYING AND SANITISING ORGANIC WASTE MATERIAL

(71) Applicant: CRI-MAN S.P.A., Correggio (RE) (IT)

(72) Inventor: Oreste Massari, Correggio (IT)

(73) Assignee: CRI-MAN S.P.A., Correggio (RE) (IT)

( * ) Notice: Subject to any disclaimer, the term of this patent is extended or adjusted under 35 U.S.C. 154(b) by 202 days.

(21) Appl. No.: 15/524,279

(22) PCT Filed: Nov. 5, 2015

(86) PCT No.: PCT/IB2015/002073
§ 371 (c)(1),
(2) Date: May 4, 2017

(87) PCT Pub. No.: WO2016/071750
PCT Pub. Date: May 12, 2016

(65) Prior Publication Data
US 2017/0314855 A1 Nov. 2, 2017

(30) Foreign Application Priority Data

Nov. 6, 2014 (IT) .............................. RE2014A0090

(51) Int. Cl.
F26B 9/08 (2006.01)
C02F 1/02 (2006.01)
(Continued)

(52) U.S. Cl.
CPC .............. *F26B 9/085* (2013.01); *A61L 11/00* (2013.01); *C02F 1/02* (2013.01); *C02F 11/12* (2013.01);
(Continued)

(58) Field of Classification Search
CPC .. F26B 9/085; F26B 3/14; F26B 11/14; F26B 21/12; F26B 2200/02; C02F 1/02;
(Continued)

(56) References Cited

U.S. PATENT DOCUMENTS 3,527,642 A * 9/1970 Cochrane ............... A23K 10/26
426/519
3,971,306 A * 7/1976 Wiese ..................... C11B 13/00
99/348

(Continued)

FOREIGN PATENT DOCUMENTS

BR PI0711129 A2 * 8/2011 ......... B02C 18/0084
CA 2651056 C * 10/2013 ......... B02C 18/0084

(Continued)

Primary Examiner — Stephen M Gravini
(74) Attorney, Agent, or Firm — Browdy and Neimark, PLLC

(57) ABSTRACT

A device (1) for drying and sanitising organic waste materials, comprising a container body (10) for housing the waste materials to be dried and provided with an inlet (16) for the materials to be dried and an outlet (17) for the dried materials, mixing elements (20) located in the container body (10) and provided with at least a blade (21) able to mix the materials to be dried and sanitised, projectingly supported by a rotating shaft (23), a ventilation circuit (30) able to generate a forced ventilation of air internally of the container body (10), and comprising generator means (33) of an air flow located externally of the container body (10) communicating with at least a dispenser nozzle (34) located internally of the container body (10), in which the at least a dispenser nozzle (34) is associated to the at least a blade (21) able to mix the waste materials located in the container body (10) wherein it comprises at least a temperature sensor (42) configured such as to measure a temperature internally of the container body (10) and in that it comprises a control system which receives a signal from the at least a temperature sensor (42) and is able to control the air flow injected into the container body (10) by the ventilation circuit (30) as a function of the signal received from the temperature sensor (42).

11 Claims, 4 Drawing Sheets

(51) Int. Cl.
    *C02F 11/12*     (2019.01)
    *C02F 11/18*     (2006.01)
    *F26B 3/14*     (2006.01)
    *F26B 11/14*     (2006.01)
    *A61L 11/00*     (2006.01)
    *F26B 21/12*     (2006.01)
    *G01K 3/00*     (2006.01)
    *C02F 103/20*     (2006.01)

(52) U.S. Cl.
    CPC .............. *C02F 11/185* (2013.01); *F26B 3/14* (2013.01); *F26B 11/14* (2013.01); *F26B 21/12* (2013.01); *G01K 3/005* (2013.01); *C02F 2103/20* (2013.01); *C02F 2209/02* (2013.01); *C02F 2303/02* (2013.01); *C02F 2303/04* (2013.01); *F26B 2200/02* (2013.01)

(58) Field of Classification Search
    CPC .... C02F 11/12; C02F 11/185; C02F 2103/20; C02F 2209/02; C02F 2303/02; C02F 2303/04; G01K 3/005
    USPC .......................................................... 34/497
    See application file for complete search history.

(56) References Cited

U.S. PATENT DOCUMENTS

| | | | |
|---|---|---|---|
| 4,831,748 A | | 5/1989 | Del Valle et al. |
| 4,927,653 A | * | 5/1990 | Manvell ............... A23B 7/0053 426/399 |
| 5,702,746 A | * | 12/1997 | Wiik ........................ A23B 4/03 426/248 |
| 8,061,056 B2 | * | 11/2011 | Hedberg .................. B01D 1/14 118/320 |
| 8,603,558 B1 | * | 12/2013 | Almutairi ................. A23L 3/16 426/233 |
| 8,657,216 B2 | * | 2/2014 | Bu ....................... B02C 18/0084 241/14 |
| 9,675,907 B2 | * | 6/2017 | Deskins .................... C05F 7/00 |
| 2011/0030235 A1 | * | 2/2011 | Brancuzsky ............... F23G 5/46 34/384 |
| 2017/0314855 A1 | * | 11/2017 | Massari .................... C02F 1/02 |

FOREIGN PATENT DOCUMENTS

| | | | | |
|---|---|---|---|---|
| DE | 4220143 A1 | | 12/1993 | |
| EP | 0606810 A1 | | 7/1994 | |
| JP | 5187772 B2 | * | 4/2013 | ......... B02C 18/0084 |
| WO | 2011114357 A1 | | 9/2011 | |
| WO | WO-2013063107 A1 | * | 5/2013 | ............... C05F 7/00 |
| WO | WO-2016071750 A1 | * | 5/2016 | ............... C02F 1/02 |

* cited by examiner

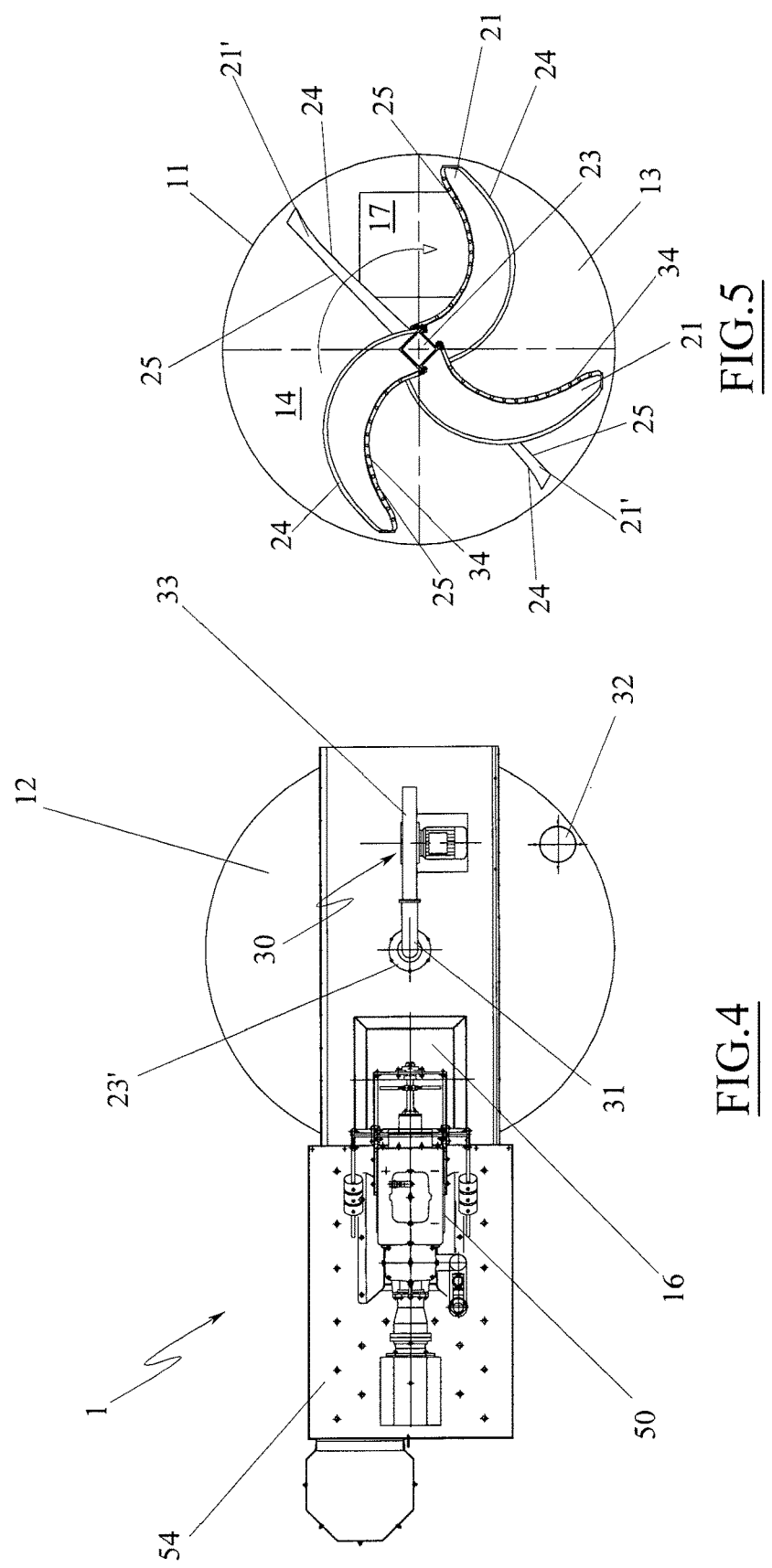

DEVICE FOR DRYING AND SANITISING ORGANIC WASTE MATERIAL

TECHNICAL FIELD

The present invention relates to a device for drying and sanitising organic waste materials and a drying and sanitising method of the organic waste materials by means of the device.

In particular, the invention relates to a device for drying and sanitising organic waste materials produced by agricultural businesses in general and livestock holdings in particular.

PRIOR ART

As is known, plants and devices for treatment of organic waste materials are progressively more common, the waste materials being produced by businesses such as for example agricultural businesses, in particular livestock holdings.

These productive companies produce a considerable quantity of organic waste materials such as for example manure, waste liquids and vegetable waste which necessarily must be eliminated.

An efficient way to eliminate these waste materials is to use them for creating useful products such as, for example, biogas for supplying internal combustion engines, compost for fertilizing land and recyclable material such as stall bedding, which can be used in the same holding or can be sent on to third parties.

The waste material, produced in particular from holdings, is normally constituted by a solid fraction and a liquid fraction.

The solid fraction of the waste material, in particular, can be used for the production of compost usable in the fertilising of agricultural land or for recycling in stall bedding.

The treatment of these waste materials includes the use of drying devices for removal of the residual moisture and for activation of the aerobic digestion of the material by the microorganisms already present in the waste material. Further, thanks to the elimination of the bacterial load the dried and sanitised material can be used as a recycling material in a stall without causing any infection to the animals.

The known drying devices comprise a container body able to receive the waste materials to be dried and provided with an inlet for the materials to be dried and an outlet for the dried materials, as well as mixing elements, able to shake and mix the waste materials housed in the container body. The container body comprises a ventilation circuit able to set the outside of the container body in fluid communication with the inside of the container body and able to generate a forced air ventilation internally of the container body.

In the known devices the mixer elements comprise means for rotating the container body, which usually exhibits a cylindrical shape and which by rotating about the axis thereof maintains the waste material to be dried in an agitated state.

In the known devices the ventilation circuit comprises a fan, for injecting air internally of the containing body, via a nozzle realised on a wall of the container body.

In this way, the material to be dried, constantly shaken and mixed, is aerated and oxygenated to facilitate aerobic digestion thereof by microorganisms, with a consequent development of heat and elimination of the bacterial load. The known devices are not however free of drawbacks, which limit efficiency thereof, reduce the quality of the product obtained and compromise use and diffusion thereof.

In particular, the ventilation circuit of the known devices is not able to guarantee an adequate and homogeneous oxygenation of the waste material and the microorganisms, so that it is not always possible to reach adequate temperatures for the aerobic digestion of the whole material undergoing drying. Therefore, the product obtained is often not homogeneously dried and only partially decomposed.

To obviate this drawback, devices are known for drying and sanitising, heated for example by exploiting the discharge fumes of cogeneration plants in the internal combustion motors in which the biogases produced by the decomposition of the liquid fraction of the waste materials are used.

These plants are however very complex and expensive to realise and require production of biogas from the liquid fraction of the waste, and are consequently suitable only for livestock holdings and large-dimension production facilities.

Furthermore, when the aerobic digestion is activated, the air blown in the container body (normally at room temperature) undergoing drying, cools down the dried material and the temperature inside the container decreases. However, the temperature drop leads to a decreasing of the sanitizing capability and, in particular, of the capability of elimination of the bacterial load.

An aim of the present invention is to obviate the above-mentioned drawbacks in the prior art, with a solution that is simple, rational and relatively inexpensive.

The aims are attained by the characteristics of the invention reported in the independent claim. The dependent claims delineate preferred and/or particularly advantageous aspects of the invention.

DESCRIPTION OF THE INVENTION

In an embodiment of the invention, in particular, a device is disclosed for drying and sanitising organic waste materials, comprising a container body for housing the waste materials to be dried and provided with an inlet for the materials to be dried and an outlet for the dried materials, mixing elements located in the container body and provided with at least a blade able to mix the materials to be dried and sanitised, projectingly supported by a rotating shaft, a ventilation circuit able to generate a forced ventilation of air internally of the container body, and comprising generator means of an air flow located externally of the container body communicating with at least a dispenser nozzle located internally of the container body, in which the at least a dispenser nozzle is associated to the at least a blade able to mix the waste materials located in the container body.

According to the invention, the device comprises at least a temperature sensor configured such as to measure the temperature internally of the container body.

In this way, the internal temperature in the device can be monitored during the treatment of the waste material to guarantee that a correct drying and effective sanitizing are attained.

Furthermore, the device comprises a control system which receives a signal from the at least a temperature sensor and is able to control the air flow injected into the container body by the ventilation circuit as a function of the signal received from the temperature sensor.

In this way, a device is provided in which it is possible to control the internal temperature of the container body during the drying action, ensuring that the material obtained is adequately dried and sanitized.

In a further aspect of the invention, the rotating shaft is a hollow shaft a cavity of which is in fluid communication with generator means of the air flow, and with at least a dispenser nozzle.

With this solution, the mixing elements are easy to design and realise, and furthermore the rotating shaft constitutes a passage conduit for the air blown internally of the container body and, consequently, the ventilation circuit is also a simple design.

In a further aspect of the invention, the at least a blade comprises a cavity in which at least a nozzle opens, and which communicates with the inside of the hollow rotating shaft.

In this way, the at least a nozzle of the ventilation circuit is constantly immersed in the mass of material to be dried and, further, the fact it is drawn in rotation by the at least a blade guarantees a correct ventilation of all the mass of material.

Further, in this way the device guarantees a more homogeneous mixing and oxygenation of the mass of material to be dried such as to obtain a more efficient drying and sanitization.

The invention is also simple and economical to make.

In a further aspect of the invention, the mixing elements comprise rotation activating means of the rotating shaft.

In the invention, the at least a nozzle is further associated to a surface of the at least a blade opposite the rotation direction of the at least a blade and is able to inject air into the container body in an opposite direction to the rotation direction of the at least a blade.

In this way, the at least a nozzle is able to blow air onto the material as soon as it is moved by the respective blade and which is therefore more greatly exposed to oxygenation so as to guarantee a more effective drying and sanitising.

In a further aspect of the invention, the mixing elements comprise a plurality of blades, and in that the ventilation circuit comprises more than one dispenser nozzle associated to a same blade.

In this way, the device guarantees a more effective agitation and homogenization of the mass of waste material in the container body.

In a further aspect of the invention, the blades are longitudinally distanced from one another along the rotation axis.

The blades are also angularly distanced from one another.

In this way, in use, the blades are distributed internally of the mass of waste material and guarantee a correct and homogeneous movement of the mass.

In this way, a device is provided in which it is possible to control the internal temperature of the container body during the drying action, ensuring that the material obtained is adequately dried and sanitized.

Moreover, the device comprises a plurality of temperature sensors configured so as to detect the internal temperature of the container body at different heights.

In this way, it is possible improve the temperature measurement internally of the container body.

In a further aspect of the invention, the device comprises gravimetric sensors able to measure the weight of the material contained in the container body.

In this way, it is possible to monitor a further parameter internally of the container body so as to establish the completion of the drying and sanitizing process.

Furthermore, the control system is able to receive a signal from the gravimetric sensors and is able to control the air flow injected into the container body by the ventilation circuit as a function of the signal received from the gravimetric sensors.

In this way, it is possible to control the air flow and the drying and sanitizing conditions on the basis of a parameter which gives information about the status of the drying and sanitizing process.

In a further aspect of the invention, the device comprises a heat exchanger for heating the air to be blown internally of the container body.

In this way, it is possible to inject heated air into the container body so as to improve the drying capability of the air itself.

Moreover, heat exchanger is configured such as to enable the heat exchange between the fumes in outlet from the container body and the air introduced internally of the container body.

In this way, it is possible to improve the efficiency of the device.

Furthermore, the heat exchanger comprises a recycling conduit associated to a outlet conduit of the fumes in outlet from the container body, the recycling conduit being coaxially inserted in an aspirating conduit, of the air introduced internally of the container body, associated to the delivery of the generator means, for heating the air introduced internally of the container body.

In this way, the heat exchange is made possible by a solution simple and economical to make.

The invention further discloses a drying and sanitising method of organic waste materials implementing a drying device, comprising steps of: introducing a certain quantity of waste material to be treated in a container body; mixing a product to be treated using at least a blade rotating about an axis; introducing a continuous air flow into the container body; measuring the temperature at least at a point internal of the container body; verifying that the temperature is within a predefined range; regulating the air flow injected into the container body through the at least a dispenser nozzle for maintaining the temperature internal of the container body internally of the predefined range. In this way, a drying and sanitising method is provided with ensures obtaining the material in an adequately dried and sanitised state.

In a further aspect of the invention, the temperature range must preferably be comprised between 40° C. and 80° C.

Further, according to the invention, in the method, before being introduced into the container, the waste materials are subjected to a separating operation of the solid part, which is subjected to treatment, from the liquid part, which is directed to other uses or are eliminated in a different way.

BRIEF DESCRIPTION OF THE DRAWINGS

Further characteristics and advantages of the invention will emerge from a reading of the description that follows, provided by way of non-limiting example, with the aid of the figures of the accompanying tables.

FIG. 4 is a view from above of the device of FIG. 3.

FIG. 5 is section V-V of FIG. 1.

BEST WAY OF CARRYING OUT THE INVENTION

Figure 1:
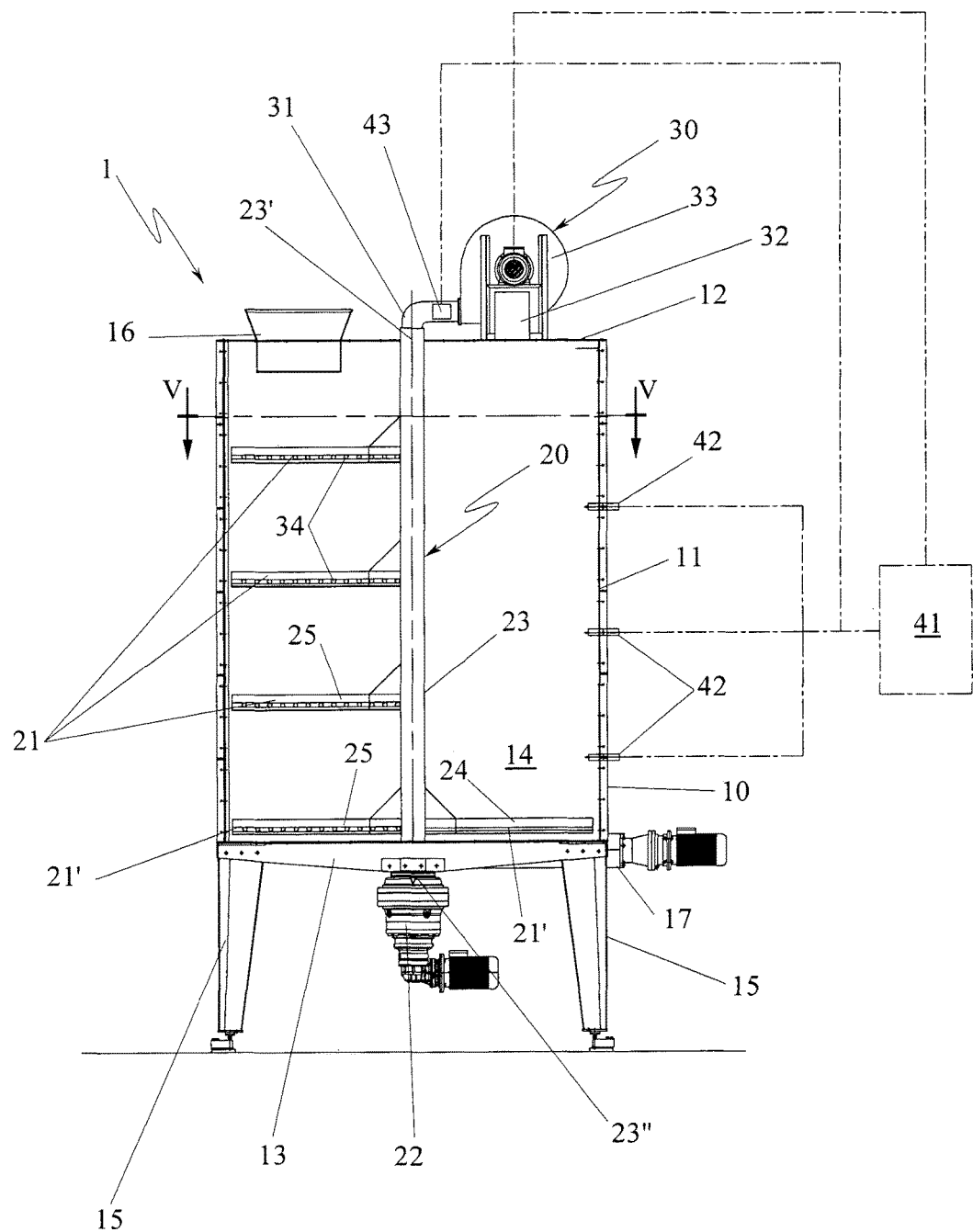
FIG. 1 is a front view of the device with a cutaway of the inside of the device.

With reference to the figures of the drawings, 1 denotes in its entirety a device for treating organic waste material.

In particular, the device 1 is for drying organic waste materials, prevalently solid, such as for example bedding and straw or other vegetable substances. The device 1 comprises a container body 10 for collecting the waste materials to be dried, in which mixing elements 20 are located, able to agitate and mix the waste materials collected in the container body.

The device 1 further comprises a ventilation circuit 30 able to set the outside of the container body 10 in fluid communication with the inside thereof, and able to generate a forced air ventilation internally of the container body.

In the preferred embodiment shown in the figures, the container body 10 is cylindrical with a substantially vertical axis.

In particular, the container body 10 comprises, for example, a lateral wall 11 having a cylindrical development, an upper wall 12 and a lower wall 13, in which the upper and lower walls 12, 13 are associated to the opposite longitudinal ends of the lateral wall 11 so as to define an internal chamber 14 for containing the material to be dried.

The container body 10 is provided with rest feet 15, associated to the lower wall 13, able to support the container body.

The container body 10 further comprises an inlet 16 for supplying materials to be dried in the internal chamber 14, and an outlet 17 for extracting the dried material from the internal chamber 14.

In the embodiment shown in the figures, the inlet 16 is advantageously fashioned in the upper wall 12, while the outlet 17 is fashioned in the lower wall 13 of the container body 10.

In this way, the material can be supplied into the internal chamber 14, through the inlet 16, and can be extracted from the internal chamber through the outlet 17 by force of gravity with no need for advancing means of the material into the internal chamber 14 from the inlet 16 towards the outlet 17. The inlet 16 is, for example, made in an offset position with respect to the axis of the container body 10.

In particular, the inlet 16 can comprise, for example, a hopper or other loading devices of known type in the sector which enable supply, in controlled quantities, of waste material into the device 1.

Further, the inlet 16 can advantageously comprise a hatch door, a cover or any other closing element able to prevent undesired access to the internal chamber 14 when the device 1 is in use or at rest, so as to prevent contamination in the internal chamber and limit the dispersion of heat during the drying of the waste materials.

Likewise, the outlet 17 comprises a hatch door, cover or any other closing element able to prevent undesired access to the internal chamber 14, so that the material accumulates on the lower bottom wall 12 and can be extracted when the drying is complete and, further, the dispersion of heat though the lower bottom door 12 is limited.

The outlet 17 comprises extraction means, known in the sector, such as a radial endless screw, which enable extracting dried and sanitised waste materials from the container body 10 in controlled quantities.

The mixing elements 20 are located in the container body 10, which mixing elements 20 are provided with at least a blade 21 that can be immersed in the waste material to be dried and are activatable in rotation about a predefined rotation axis thanks to activating means 22 in rotation of the at least a blade 21.

In particular, the at least a blade 21 is able to rotate about a longitudinal axis of the container body 10 defined by a rotating shaft 23 from which the at least a blade 21 branches.

In the embodiment shown in the figures, the mixing means 20 comprise a plurality of blades 21, for example three in number.

Each blade 21 is provided with an elongate body, for example having a circular or polygonal section, substantially arc-shaped and fixed projectingly from the rotating shaft 23 at a hole thereof.

For example, the body of each blade 21 protrudes radially from the rotating shaft 23 along a substantially perpendicular direction with respect of the rotating shaft 23 axis.

In greater detail, each blade 21 comprises a front surface 24 and an opposite rear surface 25 which lie on an incident plane to the advancement direction of the blade (indicated by the arrow in the figures).

In particular, the front surface 25 defines an advancement front of the blade 21 while the rear surface 24 is opposite the advancement direction of the blade.

In greater detail, at least a dispenser nozzle 34 is located on the rear surface 24 of each blade 21, the functioning of which will be more fully described in the following.

Each blade 21 is entirely hollow and is placed in fluid communication with the rotating shaft 23, also hollow, by means of a suitable hole fashioned thereon, and with the ventilation circuit 30, as will be more fully discussed in the following.

Each blade 21 has a length that is substantially equal to the radius of the internal chamber 14.

The blades 21 are uniformly and longitudinally distributed along the rotation axis.

In particular, the blades 21 are associated to the rotating shaft 23 in different positions distant from one another along the rotation axis.

Further, as shown in FIG. 5, the blades 21 are, in plan view, angularly distanced from one another.

In the illustrated example, the blades 21 are arranged in such a way as to occupy a circular section of 180°, while in other embodiments the blades might be angularly equidistant one from another.

In the embodiment shown in the figures, the mixing means 20 comprise a pair of further blades 21' located in proximity of the lower wall 13 of the container body 10, and fixed to the rotating shaft 23 in diametrically opposite positions from one another.

In particular, the pair of further blades 21' is located substantially in contact with the lower wall 13 so as to function as a scraper and aid the emptying of the internal chamber 14 at termination of drying.

The rotating shaft 23 exhibits a first and a second longitudinal end 23', 23", respectively associated to the upper wall 12 and to the lower wall 13 of the container body.

In particular, the first longitudinal end 23' projects from the upper wall 12 of the container body 10 and is connected, by interposing a suitable joint, to the ventilation circuit 30, as will be more fully described in the following.

Further, the second longitudinal end 23" projects from the lower part 13 of the container body 10 and is mechanically rotatingly connected to the activating means 22, for example an electric motor, of the mixing elements 20.

The rotating shaft 23 is internally hollow and is placed in fluid communication with the ventilation circuit 30 via the first longitudinal end 23' as will be more fully described in the following.

The ventilation circuit 30 comprises an inner conduit 31 of the air internally of the rotating shaft 23 and an outlet conduit 32 of the air externally of the container body 10.

The inlet conduit 31 is inserted internally of the first longitudinal end 23' of the rotating shaft 23 by interposing of a joint in such a way that the rotating shaft 23 can sealedly rotate with respect to the inlet conduit 31.

The outlet conduit 32 is, for example, defined by a chimney that branches from the upper wall 12 of the container body 10 and sets the internal chamber 14 of the container body 10 in fluid communication with the external environment.

In particular, an extraction fan, of known type and not illustrated in the figures, is associated to the outlet conduit 32, for forced aspiration of the fumes in outlet from the container body 10 and in use enables evacuation of the vapours produced by the drying and digestion of the materials of organic waste.

Further, filters can be associated to the outlet conduit 32 for removing the particulate, pollutants and/or odours from the vapours in outlet, the filters not being illustrated as of known type.

The ventilation circuit 30 also comprises a fan 33 associated to the inlet conduit 31 and able to generate a forced air ventilation internally of the container body 10.

Figure 2:
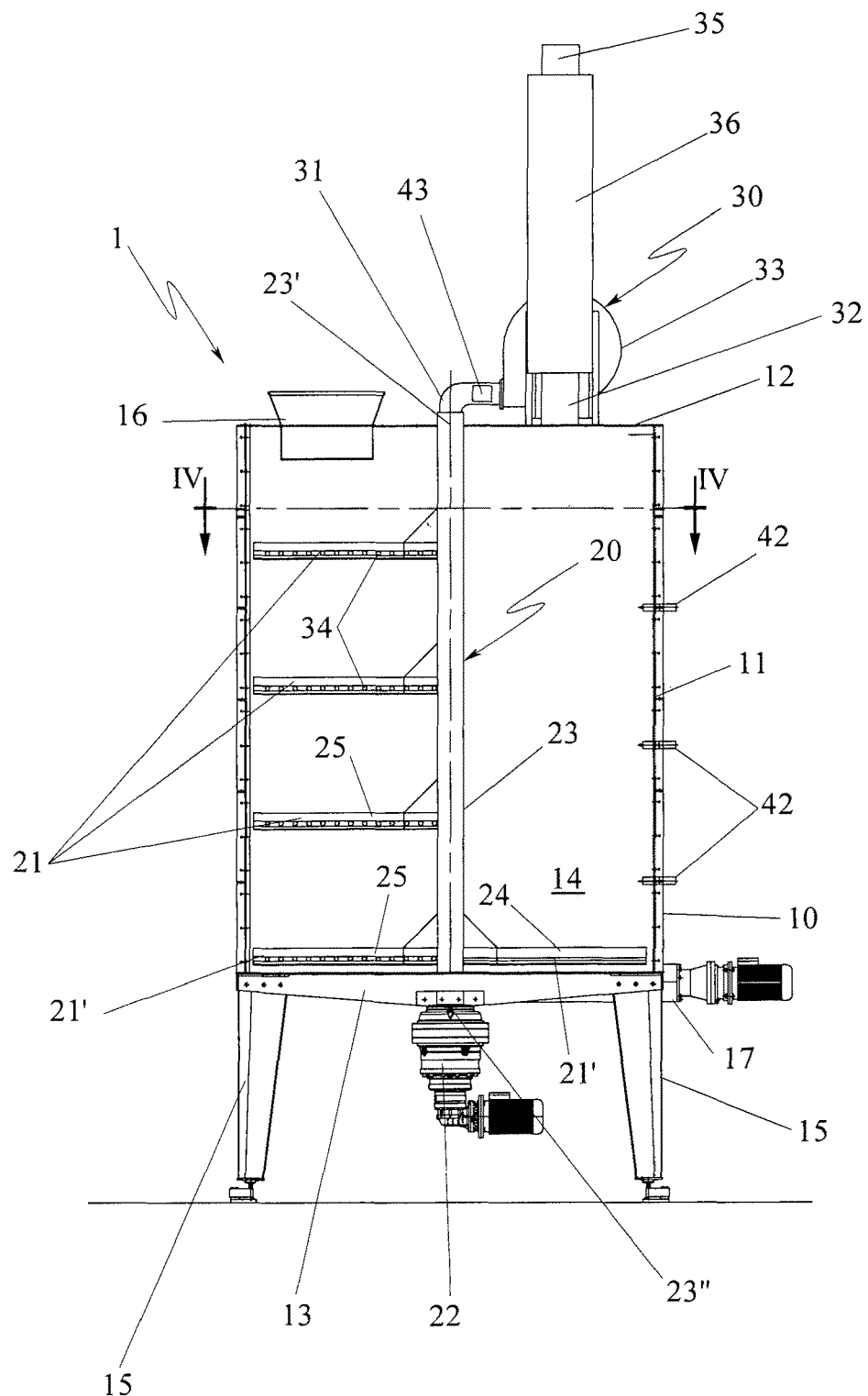
FIG. 2 is a front view of the device comprising a heat exchanger associated to the ventilation circuit.
Figure 3:
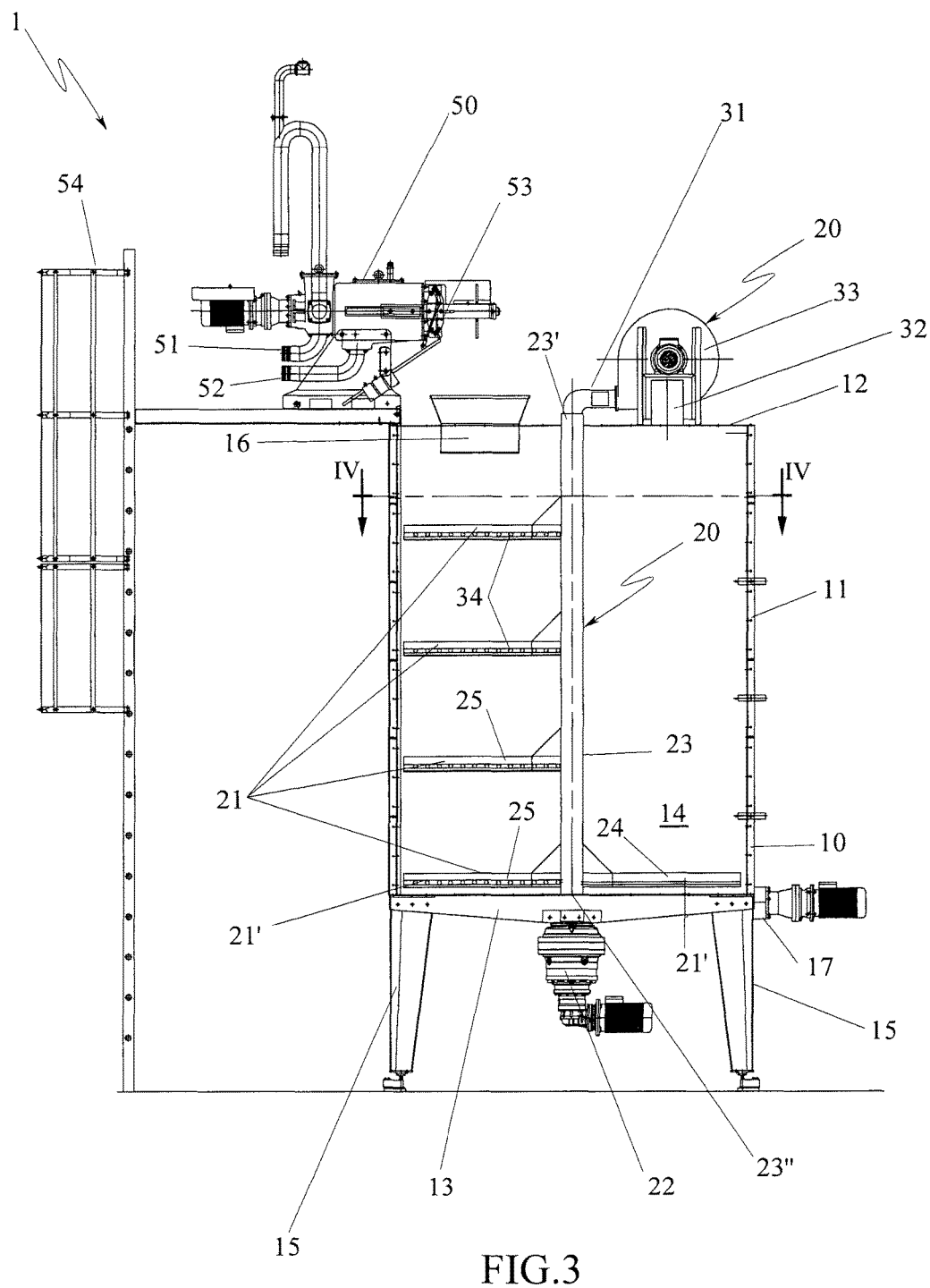
FIG. 3 is a front view of the device comprising a mechanical separating device upstream.

FIG. 2 shows an embodiment in which the ventilation circuit 30 comprises a heat exchanger 35, 36 for heating the air to be blown internally of the container body 10.

In particular, the outlet conduit 32 is associated to a recycling conduit 35, which is coaxially inserted in an aspirating conduit 36 associated to the delivery of the fan 33 for heating the air introduced internally of the container body 10.

In this way, the fan 33 aspirates air from outside the container body 10 through the aspirating conduit 36 and injects it internally of the container body 10; in the passage internally of the container body 36, the aspirated air is heated by contact with the recycling conduit 35 in which the fumes are conveyed at a high temperature, in outlet from the container body.

With the introduction of the heated air into the container body 10, the activity of the microorganisms is accelerated to facilitate the drying and sanitising of the waste material internally of the container body 10. In particular, the ventilation circuit 30 is able to inject a flow of forced air internally of the container body 10 by means of the at least a nozzle 34 associated to the blade 21.

The ventilation circuit 30 advantageously comprises a plurality of nozzles 34, for example, at least a nozzle 34 for each blade 21.

The ventilation circuit 30 preferably comprises a plurality of nozzles 34 for each blade 21.

For example, in the embodiment shown in the figures, each blade 21 comprises a plurality of nozzles 34 arranged adjacent to each other along the longitudinal direction of the blade 21 itself, that is arranged radially with respect of the rotating shaft 23 axis.

In particular, each nozzle 34 can place the internal cavity of the respective blade 21 in fluid communication with the outside of the blade 21.

In the embodiment shown in the figures, each nozzle 34 is defined substantially by a hole realised in the rear surface 25 of the respective blade 21.

With this configuration, the ventilation circuit is able to aspirate air from outside the container body 10 and injects it internally thereof through the inlet conduit 31 by means of the fan 33 associated thereto; the air then passes from the inlet conduit 31 through the internal cavity of the rotating shaft 23, and then through the internal cavity of the blade 21 then to be injected into the internal chamber 14 by means of the nozzles 34; in the internal chamber 14, in use, the air contributes to the drying of the waste materials, becoming enriched in vapours and other substances (as will be more fully described in the following) and is expelled from the container body through the outlet conduit 32.

The device 1 is provided with a control system, comprising a control card 41 connected to the fan 33 of the ventilation circuit 30 for controlling the activation and rotation velocity thereof.

The control system of the device 1 further comprises at least a temperature sensor 42, connected to the control card 41, for measuring the temperature internally of the container body 10.

In the illustrated embodiment, the control system comprises a plurality of temperature sensors 42, for example three in number, positioned in the container body 10 so as to detect the internal temperature of the chamber 14 at different heights.

The control system can advantageously also comprise a flow rate sensor 43, connected to the control card 41 and configured such as to measure the air flow rate of the air injected into the container body 10.

For example, the flow rate sensor can be realised by a Pitot tube or an anemometer installed downstream of the fan 33 and able to measure the delivery flow rate of the fan 33.

As mentioned in the foregoing, the device 1 as it is described above can treat material comprising a solid and moist fraction suitable for drying and sanitising, and a liquid fraction.

Therefore, the drying device 1 can be associated to a mechanical separating device 50, of known type, able to separate the solid fraction from the liquid fraction of the waste materials.

In particular, the mechanical separation device 50 is arranged upstream of the drying device 1 and comprises an inlet 51 for the material to be separated and a first outlet 52 for the liquid fraction of the waste material and a second outlet 53 for the solid fraction of the waste materials.

In particular, the second outlet 53 for the solid fraction of the machine can be directly connected to the inlet 16 of the drying device 1, for supplying the material internally thereof.

For example, in the embodiment shown in the figures, the mechanical separation device 50 is fixed to the upper wall 12 of the container body 10 and is external of the container body 10.

A small platform 54 can be associated to the drying device 1, provided with a step, for inspection of the device 1 and the mechanical separation device 50 by an operator.

The functioning of the drying device 1 described in the foregoing is as follows.

The material to be treated, comprising a solid fraction and a liquid fraction, is directed, via the inlet 51, to the mechanical separation device 50, which separates the liquid fraction from the solid fraction. The liquid fraction is extracted from the mechanical separation device 50 through the first outlet 52 and directed towards, for example, storage tubs or plants for production of biogas.

The solid fraction of the material, which contains a certain degree of residual moisture, is supplied in outlet from the mechanical separation device 50, into the internal chamber 14 of the device 1 through the inlet 16.

The material is collected by force of gravity on the lower bottom wall 12 of the container body 10.

The material is advantageously able, in use, to occupy the majority of the volume of the internal chamber 14 of the container body 10, so as to maximise the productivity of the device 1, reducing the size thereof.

When the material is inserted in the internal chamber 14, the mixing elements 20 and the ventilation circuit 30 are activated to set off the aerobic action of the microorganisms, contained in the material, for drying and sanitising the material; the heat generated by the digestion reaction leads to the removal of the residual moisture of the material and consequently the drying thereof; the heat also facilitates the elimination of the bacterial load of the dried material, ensuring the sanitising and enabling re-utilisation thereof in a stall.

The temperature sensors 42 of the control system detect the temperature in the internal chamber 14 and the control system regulates the air flow rate generated by the fan 33 in such a way as to maintain the temperature in the internal chamber 14 within a predefined temperature range, preferably comprised between 40° C. and 80° C., for example between 50° C. and 70° C.

For example, as already disclosed, the heat generated by the aerobic digestion itself causes an increase in temperature inside the container body 10, but an excessive ventilation cools down the inside of the container body 10; therefore, the control system can be configured such as to slow down the air flow rate injected inside the container body when the temperature is next to (or below of) the inferior limit of the predefined temperature range, so as to avoid an excessive cooling of the material meanwhile ensuring a correct oxygenation of the material to be sanitized.

The dried and sanitised material is then extracted from the container body 10 via the outlet 17.

In particular, the device 1 can comprise gravimetric sensors, of known type and not shown, such as for example load cells, associated to the lower wall 13 of the container body 10 able to measure the weight of the material contained in the internal chamber.

The sensors for the measurement of the weight can detect the reduction of the mass of material due to the drying and, consequently, establish the completion of the drying and sanitising process for enabling extraction of the dried material.

For example, the load cells can support the rest feet 15 of the container body.

Moreover, the gravimetric sensors can be connected to the control card 41 such as to deliver to the control card 41 a signal representative of the mass measured inside the internal chamber 14.

The control card 41 is configured to process the signal received from the gravimetric sensors so as to obtain an information about the status of the drying process, and is able to control the air flow injected into the container body 10 in such a way as to maintain the temperature in the internal chamber 14 within a predefined temperature range.

For example, the control card 41 is configured to process the signal received from the gravimetric sensors in such a way as to obtain an information about the quantity of dried material with respect of the total amount of material contained inside the container body 10, and is able to control the air flow injected into the container body 10 in such a way as to dry and sanitize the material not yet dried without overcool the dried material.

For example, the control system can be configured such as to low down the air flow rate injected inside the container body when the load cells measures a decrease of mass, for example when the mass measured is below of a predetermined limit value.

Alternatively the drying and sanitising process, in particular the supply and unloading thereof, can be continuous or can be done at intervals with adjustable frequency.

For example, the control system con be configured in such a way as to allow the extraction of the dried material only when predetermined conditions for the sanitization are satisfied, for example the permanence inside the container body 10 for one hour at 70° C.

The invention as it is conceived is susceptible to numerous modifications and variants, all falling within the scope of the inventive concept.

Further, all the details can be replaced by other technically-equivalent elements.

In practice, the materials used, as well as the contingent shapes and dimensions, can be any according to requirements, without forsaking the scope of protection of the following claims.

The invention claimed is:

1. A device for drying and sanitizing organic waste materials, comprising:
a container body for housing the waste materials to be dried and comprising an inlet for the materials to be dried and an outlet for the dried and sanitized materials,
mixing elements located in the container body and provided with at least a blade able to mix the materials to be dried and sanitized, projectingly supported by a rotating shaft,
a ventilation circuit configured to generate a forced ventilation of air internally of the container body, and comprising an air flow generator located externally of the container body communicating with at least a dispenser nozzle located internally of the container body, wherein the at least a dispenser nozzle is associated with the at least a blade configured to mix the waste materials located in the container body,
at least a temperature sensor configured such as to measure a temperature internally of the container body, and
a control system which receives a signal from the at least a temperature sensor and is able to control an air flow injected into the container body by the ventilation circuit as a function of the signal received from the at least a temperature sensor.

2. The device of claim 1, wherein the control system is configured to control the air flow injected into the container body by the ventilation circuit for maintaining the temperature internal of the container body internally of a predefined range.

3. The device of claim 2, wherein the temperature range is maintained between 40° C. and 80° C.

4. The device of claim 3, wherein the temperature range is maintained between 50° C. and 70°.

5. The device of claim 1, further comprising a plurality of temperature sensors configured to detect the internal temperature of the container body at different heights.

6. The device of claim 1, further comprising gravimetric sensors configured to measure the weight of the material contained in the container body.

7. The device of claim 6, wherein the control system is configured to receive a signal from the gravimetric sensors and to control the air flow injected into the container body by the ventilation circuit as a function of the signal received from the gravimetric sensors.

8. The device of claim 1, further comprising a heat exchanger for heating the air to be blown internally of the container body.

9. The device of claim 8, the heat exchanger comprises a recycling conduit associated with an outlet conduit of fumes in outlet from the container body, the recycling conduit being coaxially inserted in an aspirating conduit of the air introduced internally of the container body, associated with a delivery of the air flow generator to heat the air introduced internally of the container body.

10. The device of claim 1, wherein the rotating shaft is a hollow shaft a cavity of which is in fluid communication with air flow generator, and with at least a dispenser nozzle.

11. The device of claim 10, wherein the at least a blade comprises a cavity in which at least a nozzle opens, and which communicates with an inside of the hollow rotating shaft.

* * * * *